United States Patent
Eno et al.

(10) Patent No.: US 6,197,050 B1
(45) Date of Patent: *Mar. 6, 2001

(54) TRANSMYOCARDIAL IMPLANT WITH COMPLIANCE COLLAR

(75) Inventors: Robert A. Eno, Plymouth; Guy P. Vanney, Blaine; Mark B. Knudson, Shoreview; Katherine S. Tweden, Mahtomedi, all of MN (US)

(73) Assignee: Heartstent Corporation, St. Paul, MN (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/152,586

(22) Filed: Sep. 14, 1998

(51) Int. Cl.[7] ........................................ A61F 2/06
(52) U.S. Cl. ........................ 623/1.36; 606/151; 604/8
(58) Field of Search ...................... 623/1, 12, 1.23, 623/1.36; 606/153, 151; 604/8; 24/19

(56) References Cited

U.S. PATENT DOCUMENTS

| Re. 35,253 | * | 5/1996 | Worley et al. ............... 285/243 |
|---|---|---|---|
| 3,620,218 | * | 11/1971 | Schmitt ........................ 606/154 |
| 3,726,279 | * | 4/1973 | Barefoot et al. ............. 606/153 |
| 5,330,490 | * | 7/1994 | Wilk et al. ................... 606/153 |
| 5,399,352 | * | 3/1995 | Hanson ........................ 623/1.42 |
| 5,509,902 | * | 4/1996 | Ravlerson .................... 623/1 |
| 5,578,075 | * | 11/1996 | Dayton ........................ 623/1 |
| 5,653,755 | * | 8/1997 | Ledergerber ................ 623/8 |
| 5,755,682 | | 5/1998 | Knudson et al. . |
| 5,836,534 | * | 11/1998 | Bohmler ...................... 242/379.1 |
| 5,984,956 | | 11/1999 | Twedwn et al. . |

FOREIGN PATENT DOCUMENTS

WO 98/06356  2/1998 (WO).

OTHER PUBLICATIONS

Werker, P. et al., "Review of Facilitated Approaches to Vascular Anastomosis Surgery", *Ann Thorac Surg*, 63:S122–S127 (1997).

* cited by examiner

*Primary Examiner*—Michael J. Milano
*Assistant Examiner*—Brian E Pellegrino
(74) *Attorney, Agent, or Firm*—Merchant & Gould P.C.

(57) ABSTRACT

A transmyocardial implant includes a hollow conduit having a first portion and a second portion. The first portion is received within the lumen. The first portion has an axial dimension aligned with an axis of the vessel. The second portion is sized to extend from the vessel through the myocardium into the heart chamber. The conduit has open first and second ends on axial ends of respective ones of the first and second portions to define a blood flow pathway within an interior of the conduit between the first and second ends. A collar surrounds an exterior of the artery overlying the first portion at the first open end.

18 Claims, 4 Drawing Sheets

TRANSMYOCARDIAL IMPLANT WITH COMPLIANCE COLLAR

BACKGROUND OF THE INVENTION

1. Field of the Invention

This invention pertains to an implant for passing blood flow directly between a chamber of the heart and a coronary vessel. More particularly, this invention pertains to such an implant with an enhanced design for avoiding damage to a vessel.

2. Description of the Prior Art

Commonly assigned U.S. Pat. No. 5,755,682 and PCT International Publication No. WO 98/06356 teach an implant for defining a blood flow pathway directly from a chamber of the heart to a lumen of a coronary vessel. An embodiment disclosed in the aforementioned patent and application teaches an L-shaped implant. The implant is a conduit having one leg sized to be received within a lumen of a coronary artery and a second leg sized to pass through the myocardium and extend into the left ventricle of the heart. As disclosed in the above-referenced patent and application, the conduit remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997, now U.S. Pat. No. 5,984,956, entitled "Transmyocardial Implant", and filed in the name of inventors Katherine S. Tweden, Guy P. Vanney and Thomas L. Odland, teaches an implant such as that shown in the aforementioned '356 application and '682 patent with an enhanced fixation structure. The enhanced fixation structure includes a fabric surrounding at least a portion of the conduit to facilitate tissue growth on the exterior of the implant.

Implants such as those shown in the aforementioned patent and applications include a portion to be placed within a coronary vessel and a portion to be placed within the myocardium. When placing a portion of the implant in the coronary vessel, the vessel is incised a length sufficient to insert the implant. When placed within the coronary vessel, the implant discharges flow axially into the vessel.

When placing an implant, a portion of the coronary artery is dissected. The dissected portion is incised and the vessel portion of the implant is inserted into the lumen. A stay suture secures the artery to the implant. The stay suture is placed around the artery and vessel portion a distanced spaced from the open end of the vessel portion.

In a preferred embodiment, the implant is rigid. An artery is flexible. A pulsing and alternating flow of blood through the rigid implant and flexible vessel can result in relative movement between the implant and vessel. As a result of such movement, a rubbing action may occur with the implant causing cellular damage to the vessel. Such damage may proliferate resulting in a fibrotic response which grows to block the implant or artery.

SUMMARY OF THE INVENTION

According to a preferred embodiment of the present invention, a transmyocardial implant is disclosed for establishing a blood flow path through a myocardium between a heart chamber and a lumen of a coronary vessel residing on an exterior of the heart. The implant includes a hollow conduit having a first portion and a second portion. The first portion is received within the lumen. The first portion has an axial dimension aligned with an axis of the vessel. The second portion is sized to extend from the vessel through the myocardium into the heart chamber. The conduit has open first and second ends on axial ends of respective ones of the first and second portions to define a blood flow pathway within an interior of the conduit between the first and second ends. A collar surrounds an exterior of the artery overlying the first portion at the first open end.

DESCRIPTION OF THE PREFERRED EMBODIMENT

Figure 1:
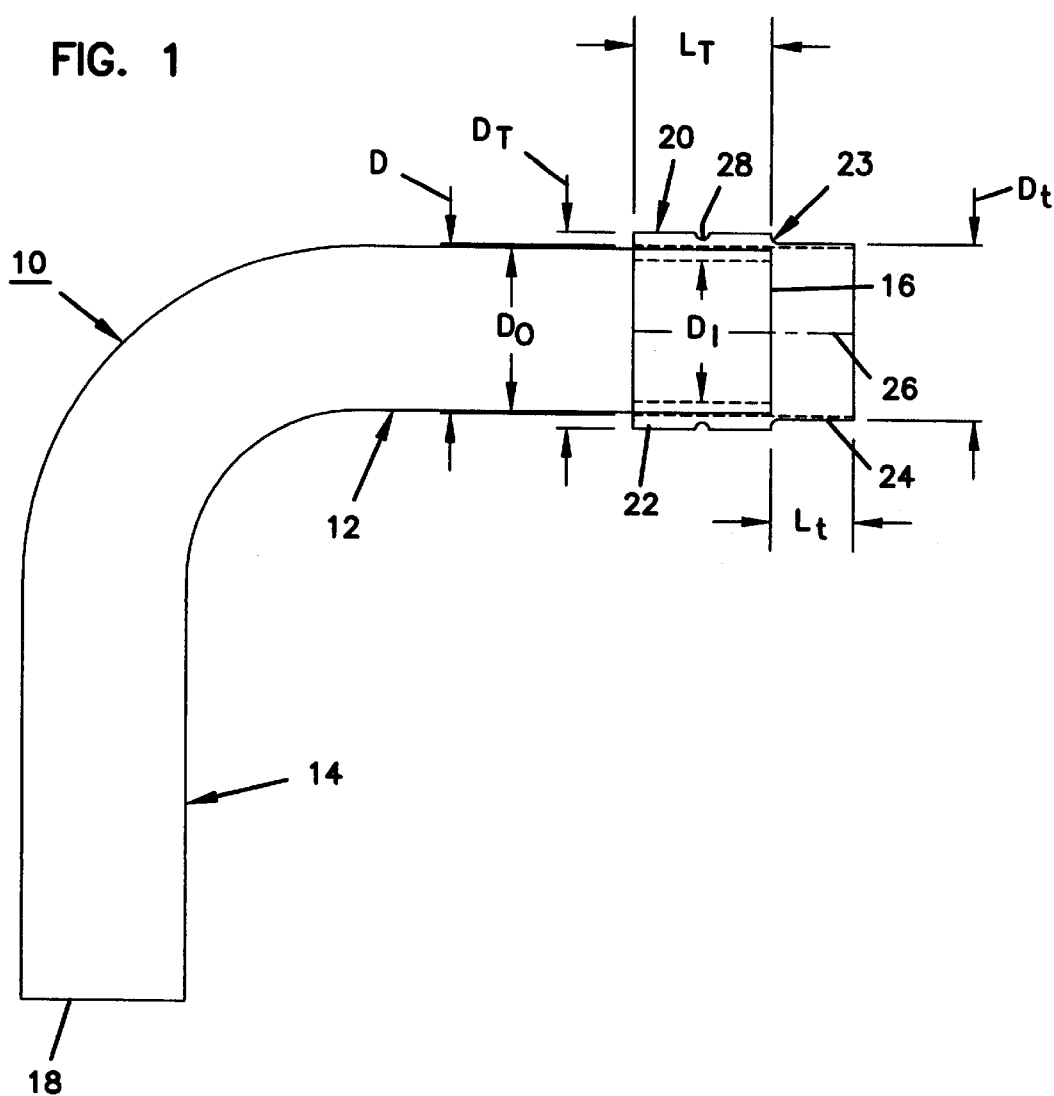
FIG. 1 is a side elevation view of a first embodiment of an implant and collar according to the present invention.

With initial reference to FIG. 1, a conduit 10 is shown in the form of an L-shaped rigid tube. The conduit 10 may be formed of titanium or other rigid biocompatible material such as pyrolytic carbon or may be titanium coated with pyrolytic carbon. The material of the conduit 10 is preferably a rigid material in order to withstand contraction forces of the myocardium. By way of example, the tube will have an outside diameter $D_O$ of about 2.5 millimeters and an internal diameter $D_I$ of about 2 millimeters to provide a wall thickness of about 0.25 millimeters.

Figure 3:
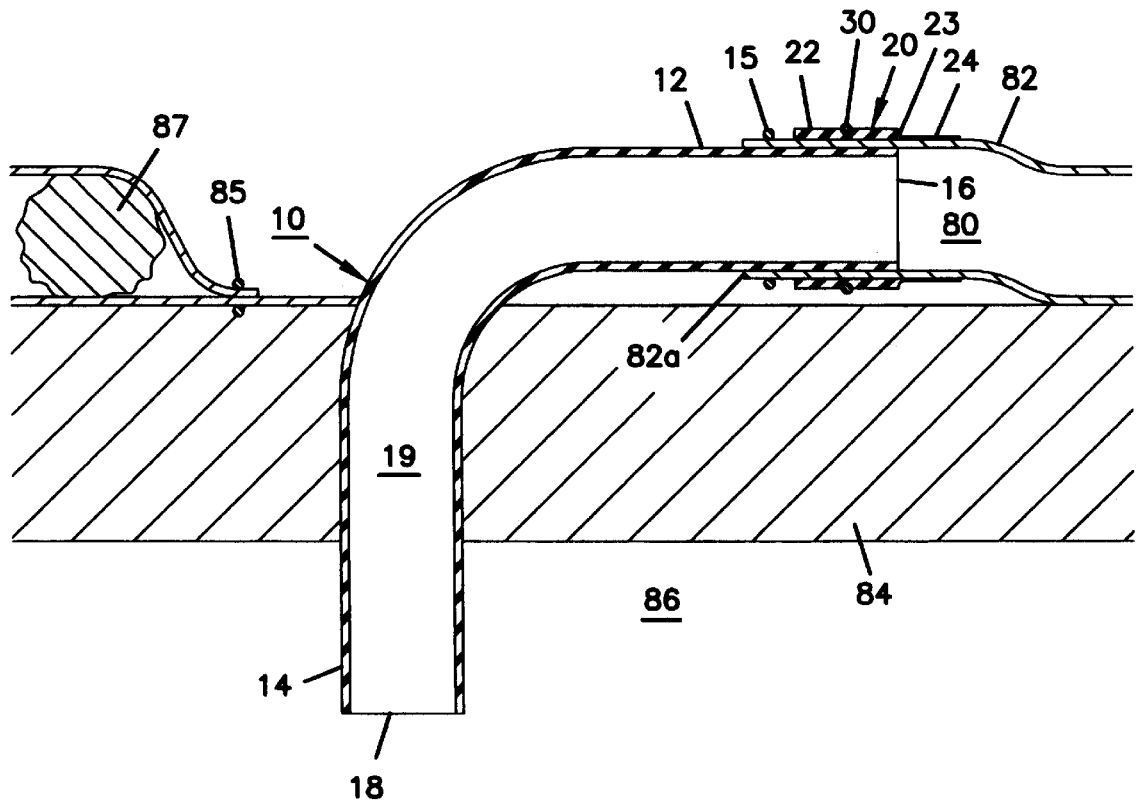
FIG. 3 is a side cross-sectional view of the implant and collar of FIG. 1 following surgical placement.

The implant 10 has a first portion (or vessel end) 12 sized to be received within the lumen of a coronary vessel such as the lumen 80 of a coronary artery 82 illustrated in FIG. 3. The conduit 10 has a second portion (or myocardium end) 14 extending at a right angle to the axis of portion 12. The second portion 14 is sized to extend from the coronary artery 82 directly through the myocardium 84 and protrude into the left ventricle 86 of a patient's heart. The second portion 14 is sized to have a length sufficient for the portion 14 to protrude into the left ventricle 86.

The vessel end 12 has a first opening 16. The myocardium end 14 has a second opening 18 in communication with an interior 19 (shown in FIG. 3) of the implant 10. Therefore, blood can freely flow through the implant 10 between the left ventricle 86 and the lumen 80 of the coronary artery 82. Blood flows axially out of opening 16 parallel with the axis of lumen 80.

As discussed more fully in the afore-mentioned commonly assigned and co-pending U.S. patent application Ser. No. 08/944,313, the portion 14 may be provided with tissue-growth inducing material (only shown in the present application in FIG. 6) such as a polyester fabric sleeve to immobilize the implant 10 within the myocardium 84.

Figure 2:
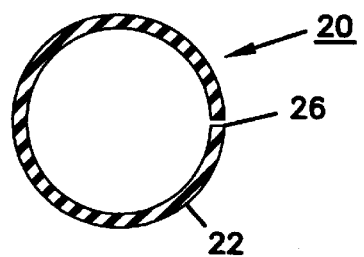
FIG. 2 is a cross-sectional view of the collar of FIG. 1.

The present invention further includes a collar 20. The collar 20 in the embodiment of FIGS. 1–3 is a tubular member having a thickened cylindrical portion 22 and co-axially aligned thinned cylindrical portion 24. The thickened and thinned portions 22, 24 are joined at a transition point 24. Preferably, the thickened and thinned portions 22, 23 are integrally formed of molded, bio-compatible material such as silicone rubber.

The thickened and thinned portions 22, 24 have a common internal diameter D sized larger than the outside diameter $D_O$ of the vessel portion 12 by an amount less than or equal to the thickness of the artery 82. An axial split line 26 is formed through the thickened and thinned portions 22, 24 to permit the collar 20 to be axially split open for placement on an artery 82 and implant 10 as will be described. The thickened portion 22 includes an annular groove 28 to receive a suture 30 to hold the collar 20 in place.

With respect to the representative dimensions given, the collar 20 has an internal diameter D of 3.0 mm. The thickened portion 22 has an external diameter $D_T$ of 5.0 mm and an axial length $L_T$ of 4.0 mm. The thinned portion 24 has an external diameter $D_t$ of 3.75 mm and an axial length $L_t$ of 3.0 mm. Preferably, the collar 20 is formed of silicon rubber having a Durometer of 30 Shore A.

In FIG. 3, the vessel portion 12 is shown residing within a coronary vessel (such as coronary artery 82). The longitudinal axis of the vessel portion 12 is aligned with the axis of the lumen 80. Sutures 15 secure the artery 82 to the vessel portion 12. The proximal portion of the coronary artery is ligated by sutures 85 distal to an obstruction 87.

When placing an implant 10, a surgeon dissects a portion of the artery 82 away from the myocardium 84. The surgeon ligates the artery 82 distal to an obstruction 87 with sutures 85. The surgeon then forms an incision through the artery 82 distal to the ligating suture 85.

The vessel portion 12 is slipped into the lumen 80 through the open end 82a of the artery 82. A stay suture 15 is placed around the artery 82 overlying the vessel portion 12.

The collar 20 is split open at the part line 26 and placed over the artery 82 at the open end 16 and overlying the vessel portion 12. The collar 20 is positioned with the thickened portion 22 overlying the vessel portion 12 and with the thinned portion 24 extending distally to the open end 16 and overlying the artery 82. The transition point 23 between the thickened and thinned portions 22, 24 is positioned flush with the open end 16. A stay suture 30 is placed in groove 28 to hold the collar 20 tightly on the artery 82 and vessel portion 12.

Since the internal diameter D of the thickened portion 22 is only 0.5 mm larger than the external diameter $D_O$ of the vessel portion 12, the artery 82 (which typically has a wall thickness of 0.25 mm or greater) is crimped onto the vessel portion 12 along the entire axial length $L_T$ of the thickened portion 22. This crimping prevents relative movement between the implant 10 and any overlying portion of the artery 82.

The thinned portion 24 provides a stiffening along the artery 82 distal to the open end 16. This reduces relative movement between the artery 82 and vessel portion 12 at the open end 16. The thinned portion 24, while stiffer than an artery 82, is still flexible to create a transition zone between the artery 82 and vessel portion 12. Effects of a compliance mismatch between the vessel portion 12 and artery 82 are distributed over a length of the artery 82 (represented by the length $L_t$ of the thinned portion 24) thereby minimizing arterial injury. Further, the thinned portion distributes forces over the exterior of the artery 82 rather than having such forces impact upon a more fragile interior surface of the artery 82.

Figure 3A:
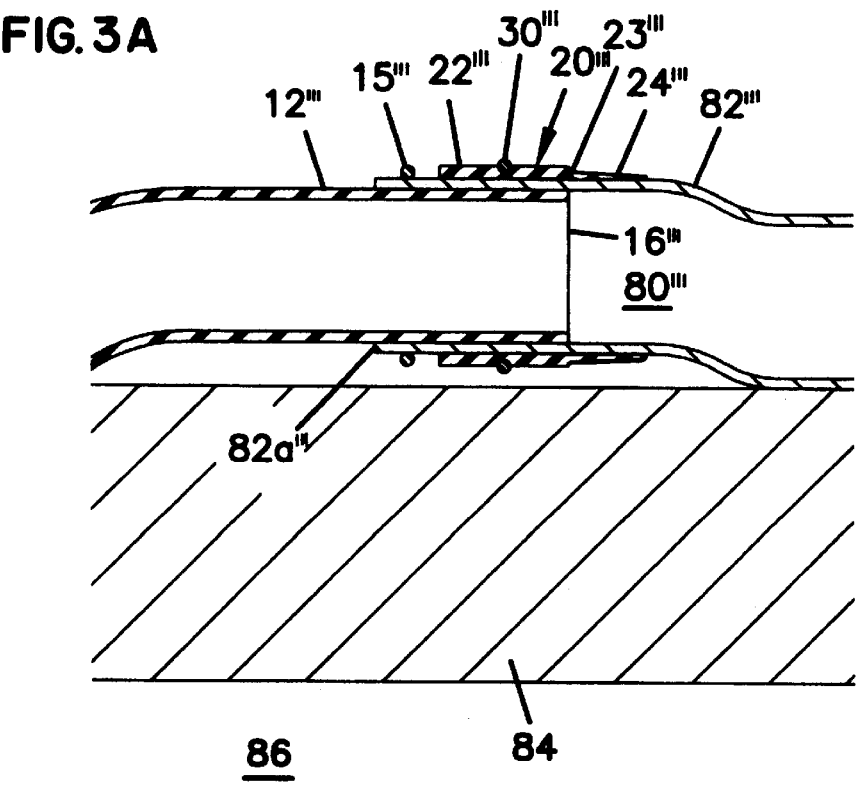
FIG. 3A is an enlargement of a portion of the view of FIG. 3 showing an alternative embodiment with an extension with varying thickness.

Numerous modifications are possible with the embodiment of FIGS. 1–3. For example, as described, the thinned portion 24 has uniform thickness and durometer along its axial length $L_t$. This results in uniform stiffness. The thinned portion 24 can be modified to vary the flexibility of the thinned portion along its length $L_t$ by, for example, varying its thickness (as shown in FIG. 3A in which elements are numbered as before but with triple apostrophes to distinguish the embodiments) or material of construction. Also, while simply placing the thinned portion 24 over an artery 82 is presently preferred, a layer of fibrotic-based adhesive can be placed between the thinned portion 24 and the artery 82. Adhering the artery 82 to the thinned portion 24 reduces relative movement between the artery 82 and vessel portion 12 and collar 20 when the artery might constrict during diastole.

An additional advantage of the embodiment of FIGS. 1–3 is to permit slight axial misalignment between the vessel portion 12 and the artery 82. The thinned portion 24 urges the artery 82 into such alignment with the resulting forces distributed over the length $L_t$ of the thinned portion 24.

Figure 4:
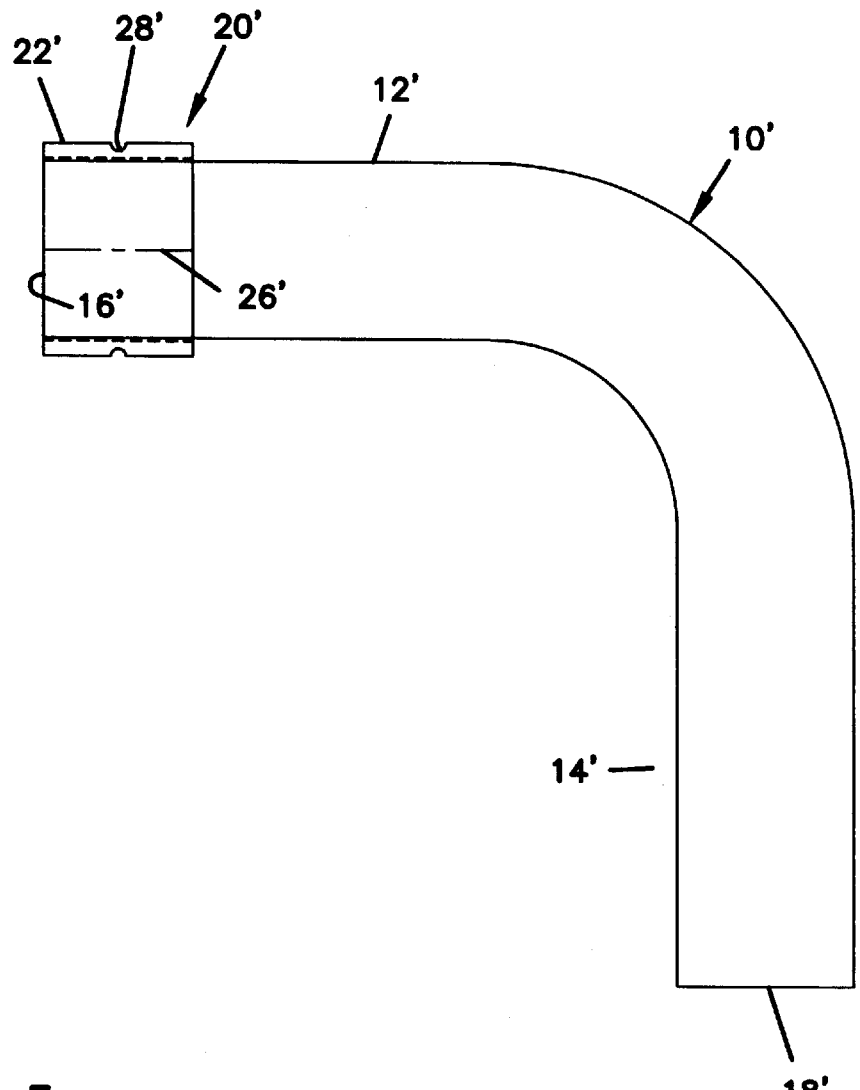
FIG. 4 is a side elevation view of a second embodiment of an implant and collar according to the present invention.
Figure 5:
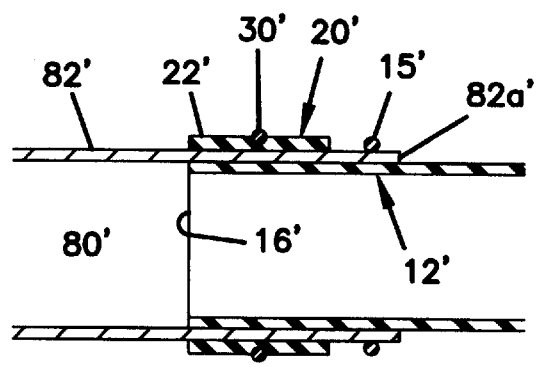
FIG. 5 is a side cross-sectional view of the implant and collar of FIG. 4 secured to a coronary vessel.

FIGS. 4–5 illustrate an alternative embodiment implant 10' (all similar elements numbered identically with the addition of an apostrophe and not separately described unless modified in the embodiment). In FIGS. 4–5, the thinned portion 24 is eliminated. The thickened portion 22' crimps the artery 82' and is flush with the open end 16'. This reduces the relative motion and transfers torque to the artery 82' at a point distal to the open end 16'.

An additional alternative is to fabricate the collar 20 in situ. For example, any one of a number of polymers in fluid form can be placed around the artery overlying the implant 10. Such polymers are cured in situ through any one of a variety of means (e.g., exposure to radiation such as light wavelengths selected to cure the polymer). Such polymers are used in practice by the Focal™ company of Massachusetts, United States. The cured polymer acts as a collar with the benefits of the present invention.

Figure 6:
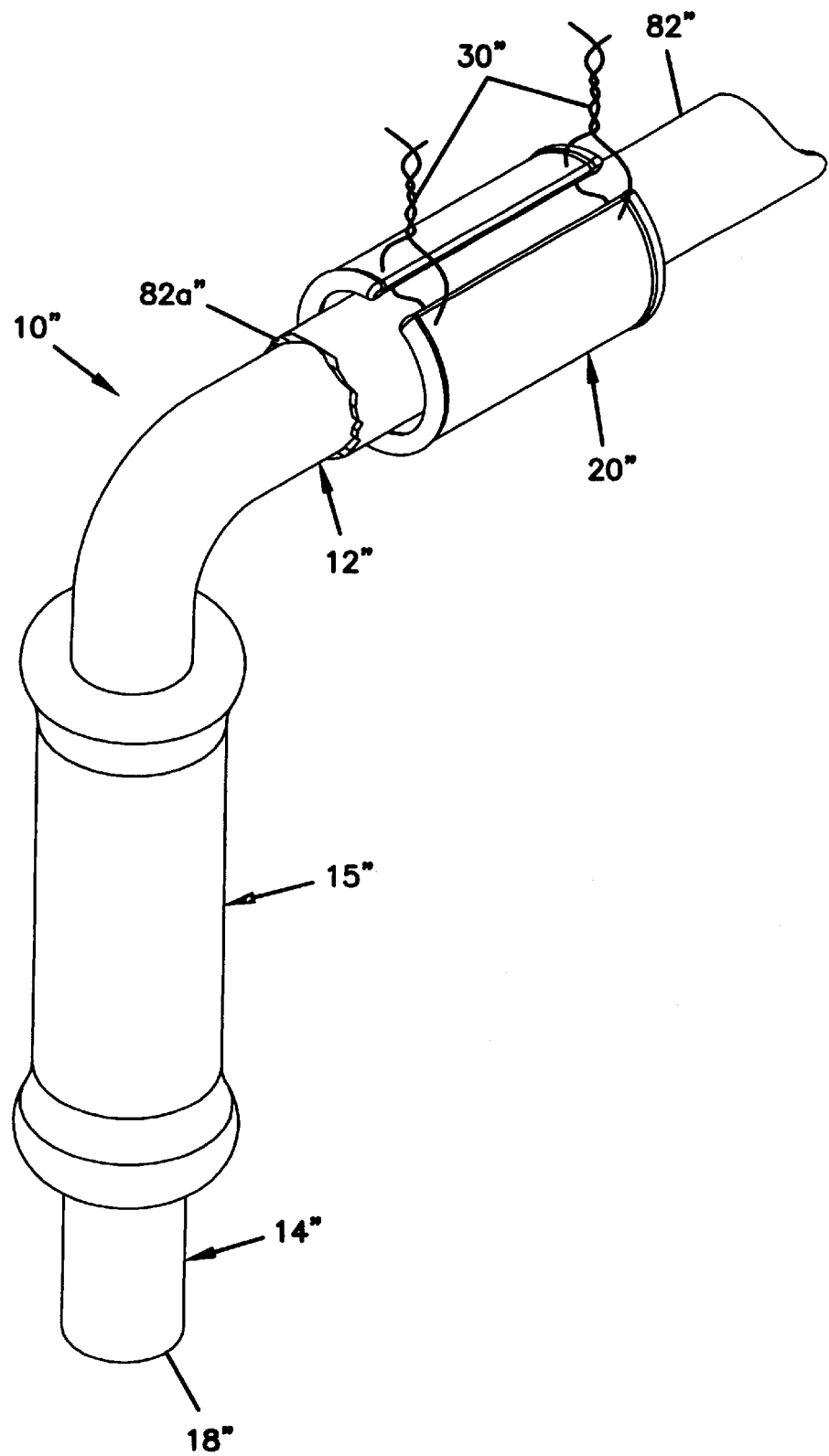
FIG. 6 is a perspective view of a third embodiment showing a vessel portion of an implant inserted within an artery and surrounded by a fabric collar.

FIG. 6 illustrates a still further alternative embodiment. In FIG. 6, all elements corresponding to those in FIG. 1 are identically numbered with the addition of a double apostrophe. Structure identical to FIG. 1 is not separately described. In FIG. 6, the second portion 14" of the implant 10" is shown provided with a polyester fabric cuff 15" to facilitate tissue in-growth as described in the afore-mentioned U.S. patent application Ser. No. 08/882,397. The first portion 12 is shown inserted into a coronary artery 82". The collar 20" is a polyester fabric sheet (e.g., a sheet of polyethylene terephthalate). The sheet 20" is formed into a cylinder surrounding the exterior of the artery 82" and overlying the vessel portion 12" at its open end. The sheet 20" preferably extends beyond the open end. The sheet 20" is tightened and secured in place by sutures 30'. Tissue may grow into the fabric 20" bonding the fabric 20" to the artery 82'.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims appended hereto.

What is claimed:

1. A transmyocardial implant for establishing a blood flow path through a myocardium between a heart chamber and a lumen of a coronary vessel residing at an exterior of said myocardium, said implant comprising:

a hollow conduit having a first portion and a second portion;

said first portion sized to be received within said lumen, said first portion having an axial dimension aligned with an axis of said vessel;

said second portion sized to extend from said vessel through said myocardium into said chamber;

said conduit having open first and second ends on axial ends of respective ones of said first and second portions to define a blood flow pathway within an interior of said conduit between said first and second ends;

said first portion formed of rigid, bio-compatible material at said open first end and sized for an interior surface of said vessel to surround said first portion at said first end;

a collar dimensioned so as to surround an exterior of the vessel overlying the first portion at the first open end, said collar formed of a material more flexible than said first portion;

said collar dimensioned so as to urge an interior surface of said vessel against an exterior surface of said first portion at said first open end, the collar overlying the first open end and including an extension that surrounds said vessel and extends axially beyond the first open end in a direction distal to the first open end.

2. A transmyocardial implant according to claim 1 wherein the collar is sized and placed to fix said vessel immobilized at the first open end.

3. A transmyocardial implant according to claim 1 wherein the first portion has a predetermined external geometry and the collar is sized to be spaced from the external geometry not greater than a thickness of the vessel.

4. A transmyocardial implant according to claim 1 wherein the collar is axially split to permit opening and placement of the collar.

5. A transmyocardial implant according to claim 1 wherein the extension has a stiffness greater than a stiffness of the vessel.

6. A transmyocardial implant according to claim 1 wherein the extension has a stiffness that varies along a length of the extension.

7. A transmyocardial implant according to claim 1 further comprising an adhesive on an interior surface of the extension for adhering an outer surface of the vessel to the extension.

8. A transmyocardial implant according to claim 1 wherein the collar is an in situ cured polymer.

9. A transmyocardial implant according to claim 1 wherein the collar is formed of a molded polymeric material.

10. A transmyocardial implant according to claim 1 wherein the collar is formed of a fabric.

11. A transmyocardial implant according to claim 1, wherein the collar includes a thickened portion that is co-axially aligned with a thinned portion.

12. The implant of claim 11, further comprising a wall thickness transition portion between the thickened portion and the thinned portion.

13. A transmyocardial implant for establishing a blood flow path through a myocardium between a heart chamber and a lumen of a coronary vessel residing at an exterior of said myocardium, said implant comprising:

a hollow conduit having a first portion and a second portion, and a first open end and a second open end on axial ends of respective first and second portions to define a blood flow pathway within an interior of said conduit between said first and second open ends;

said first portion having an axial dimension aligned with an axis of said vessel; said first portion sized to be received within the lumen and for an interior surface of the vessel to surround said first portion at said first open end;

said second portion sized to extend from the vessel through the myocardium into the heart chamber; and a collar dimensioned so as to surround an exterior of the vessel overlying said first portion at said first open end and to urge an interior surface of the vessel against an exterior surface of said first portion at said first open end;

said collar including an extension, said extension having an extension length and extending axially beyond said first open end, said extension surrounding the vessel over said extension length, said extension having a flexibility sufficient to distribute the effects of compliance mismatch between said first portion and the vessel over the vessel for a distance of said extension length.

14. A transmyocardial implant according to claim 13 wherein said collar has a flexibility greater then a flexibility of said first portion.

15. A transmyocardial implant according to claim 13 wherein said extension has a flexibility less than a flexibility of the vessel.

16. A transmyocardial implant according to claim 13 wherein said extension has a flexibility that varies along said extension length.

17. A transmyocardial implant according to claim 13 wherein said collar includes a thickened portion that is co-axially aligned with a thinned portion.

18. A transmyocardial implant according to claim 17 wherein said extension is said thinned portion.

* * * * *